United States Patent [19]

Hefner, Jr. et al.

[11] Patent Number: 5,290,887

[45] Date of Patent: Mar. 1, 1994

[54] EPOXY RESINS CONTAINING THIADIAZOLE AND/OR OXADIAZOLE MOIETIES

[75] Inventors: Robert E. Hefner, Jr., Lake Jackson, Tex.; Joseph A. Schomaker, Midland, Mich.; Jimmy D. Earls, Lake Jackson, Tex.

[73] Assignee: The Dow Chemical Company, Midland, Mich.

[21] Appl. No.: 56,699

[22] Filed: Apr. 30, 1993

[51] Int. Cl.$^5$ .................... C08G 59/00; C08G 65/08; C08G 65/14

[52] U.S. Cl. .................... 525/523; 525/533; 528/96; 528/104; 528/206; 528/208; 528/210; 528/220; 528/229; 528/321; 528/327; 528/361; 528/365; 528/367; 528/369; 528/377; 528/391; 528/403; 528/407; 549/551; 549/553; 252/299.61

[58] Field of Search ................ 528/96, 369, 365, 367, 528/407, 220, 391, 104, 206, 208, 210, 219, 321, 327, 361, 377, 403, ; 525/523, 533; 549/551, 553

[56] References Cited

U.S. PATENT DOCUMENTS

3,457,073 7/1969 Delzenne et al. .................. 96/35.1
3,903,101 9/1975 Yoshida et al. .................. 260/30.76

OTHER PUBLICATIONS

Polymer Preprints, vol. 33, No. 1, Apr. 1992, "Polyimides Containing Heterocycles: Imide-Aryl Ether Oxadiazole and Imide-Aryl Ether Benzothiazole Copolymers", James L. Hedrick.
Liquid Crystals, 1990, vol. 7, No. 4, 475-485, "Imidazo [2,1-b]-1,3,4-thiadiazoles A new class of liquid-crystalline compounds", by A. V. Ivashchenki, S. I. Torgova, L. A. Karamysheva and A. G. Abolin.
Mol. Cryst Liq. Cryst., 1989, vol. 172, pp. 51-56, "Mesogenic Semicarbazones and Amino Oxidiazoles'-'-I, N. K. Chudgar, * S. N. Shan and R. A. Vora.
Ferroelectrics, 1991, vol. 114, pp. 289-293, "New Liquid Crystalline Thiadiazole Derivatives", C. Tschierske, D. Joachimi, G. Y. Bak, H. Zaschke, B. Linstrom, H. Kresse, D. Demus.
Derwent Abstracts: 116:58641q, "The dependence of the spontaneous polarization on the Molecular Structure", Lindstroem, B.; Kresse, H.; Demus, D.; Tschierski, C.; Joachimi, D.
Ferroelectrics, 1991, 120(3-4), 225-30 (Eng).
Derwent Abstracts: 115:256184K, "Preparation of optically active thiadiazole compounds as liquid crystal compositions", Nohira, Hiroyuki; Nakamura, Shinichi; Yamada, Yoko; Takiguchi, Takao; Iwaki, Takashi, Tokano, Goji (Canon K.K).
Derwent Abstracts: 116:129931x, "Polyether-poly(1,3-,4-oxidazoles) from bis(hydroxyphenyl)-1,3,4-oxadiazoles", Connell, John W.; Hergenrother, Paul M.; Wolf, Peter.
Derwent Abstracts: 113:211992q, 2,5-Bis(4-(4-aminophenyl)phenyl]-1,3,4,-oxidazole as material for azo dyes and functional polymers, Yamada, Yasuyuki; Ito, Naoto; Nishizawa, Isao; Yamaguchi, Teruhiro (Mitsui Toatsu Chemicals, Inc.).
Derwent Abstracts: 115:21989u, "Mesomorphic compounds for liquid crystal compositions for display devices", Iwaki, Takashi; Takiguchi, Takao; Nakamura, Shinichi; Yamada, Toko; Togano, Takeshi; Mori Shosei (Canon K.K.).

(List continued on next page.)

Primary Examiner—Frederick Krass

[57] ABSTRACT

Epoxy resins containing more than one vicinal epoxide group per molecule and at least one thiadiazole, oxadiazole or both thiadiazole and oxadiazole moiety per molecule are disclosed, as well as curable and cured compositions thereof. Certain of these epoxy resins possess enantiotropic liquid crystallinity. These enantiotropic epoxy resins are useful in preparing copolymers with high glass transition temperatures and liquid crystalline morphology, which can result in enhanced unidirectional mechanical properties. These epoxy resins are useful in coating, casting, encapsulation, electronic or structural laminate or composite, filament winding or molding applications.

8 Claims, No Drawings

OTHER PUBLICATIONS

Derwent Abstracts: 115:49520b, "Synthesis of semicarbazones, oxadiazoles and evaluation of their different properties", Chudgar, N. K.; Shah, S. N.; Bapat, Sangita (Dep. Chem., M.S. Univ. Baroda, Baroda, 390002 India.) J. Inst. Chem. (India) 1990, 62(5), 185–186 (Eng.).

Derwent Abstracts: 116:13794a, "Liquid-crystal mixtures having extended smectic phases", Tschierske, Carsten; Girdziunaite, D.; Zaschke, Horst; Heinemann, Susanne; Kresse, Horst; Demus, Dietrich (Martin-Luther-Universitaet Halle-Wittenberg) Ger. (East) DD 292,267.

Derwent Abstracts: 115:185230j, "IR-spectroscopy study of structural and phase transformations in poly(-p-phenylene-1,3,4-oxidiazole) fibers under thermal actio", Belousova, T. A.; Romanko, O. I.; Kalashnik, A. T.; Banduryan, S. I.; Okromchedlidze, N. P.; Semenova, A. S.

Derwent Abstracts 116:72473t, "Electrically controlled birefringence effect-based liquid crystal compositions containing thiadiazole derivatives", Krause, Joachim; Geelhaar, Thomas; Hittich, Reinhard, Finkenzeller, Ulrich; Weber, Georg; Rieger, Bernhard (Merck Pat. G.m.b.H.).

Derwent Abstracts: 116 :162630w, "Liquid-crystal compounds and compositions and devices using them"; Nakamura, Shinichi; Yamada, Yoko; Nohira, Hiroyuki; Takiguchi, Takao; Iwaki, Takashi; Togano, Takeshi (Canon K.K.) Eur. Pat. Appl. EP 435,106.

Derwent Abstracts: 115:171041m, "Mesomorphic compounds for liquid crystal compositions for display devices", Nakamura, Shinichi; Takiguchi, Takao; Iwaki, Takashi; Togano, Takeshi; Yamada, Yoko; Mori, Shosei (Canon K.K.) Ger. Offen. DE 4,021,811.

Derwent Abstracts: 115:123933g, "Liquid crystal compositions for display devices", Togano, Takeshi; Takiguchi, Takao; Iwaki, Takashi; Yamada, Yoko; Nakamura, Shinichi; Mori, Shosei (Canon K.K) Ger. Offen. DE 4,024,190 (Cl. C09K 19/06), Feb. 7, 1991, JP.

Derwent Abstracts: 116:162662h, "Mesmorphic compound and liquid-crystal composition, device display apparatus, and display method using it", Takiguchi, Takao; Iwaki, Takashi; Togano, Takeshi; Yamada, Yoko; Nakamura, Shinichi (Canon K.K.) Eur. Pat. Appl. 455,219.

Derwent Abstracts: 115:171041m, "Mesomorphic compounds for liquid crystal compositions for display devices," Nakamura, Shinichi; Takiguchi, Takao; Iwaki, Takashi; Togano, Takeshi; Yamada, Yoko; Mori, Shosei (Canon K.K.) Ger. Offen. DE 4,021,811.

Derwent Abstracts: 115:49520b, "Synthesis of semicarbazones, oxadiazoles and evaluation of their different properties", Chudgar, N. K.; Shah, S. N.; Bapat, Sangita (Dep. Chem., M.S. Univ. Baroda, Baroda, 390 002 India). J. Inst. Chem. (India) 1990, 62(5), 185–6 (Eng.).

Derwent Abstracts: 113:115189n, "Liquid crystalline, 1,3,4-thiadiazoles, II, 1,3,4-Thiadiazoles with cyclohexane fragments", Schaefer, W.; Rosenfeld, U.; Zaschke, H.; Stettin, H.; Kresse, H. (Sekt. Chem., Martin-Luther-Univ., DDR-4010 Halle/Saale, Ger. Dem. Rep.). J. Prakt. Chem. 1989.

Derwent Abstracts: 115:124294m, "Liquid crystal composition having extended smectic C phase range", Zaschke, Horst; Girdziunaite, D.; Paschke, Reinhard; Kresse, Horst; Tschierske, Carsten; Demus, Dietrich; Linstroem, Brita (Martin-Luther-Universitaet Halle-Wittenberg).

Derwent Abstracts: 115:124299s, "Preparation of 1,3,4-thiadiazole derivatives as liquid crystals and their compositions for liquid crystal devices", Mori, Yoshimasa; Yamada, Yoko; Tokanai, Goji; Takiguchi, Takao; Iwaki, Takashi; Nakamura Shinichi (Canaon K.K.).

Derwent Abstracts: 115:219576u, "New mesogenic 1,3,4-oxadiazole derivatives", Girdziunaite, Dalia; Tschierske, Carsten; Novotna, Eva; Kresse, Horst; Hetzheim, Annemarie (Sekt. Chem., Martin-Luther Univv. Halle Wittenbert, O-4010 Halle/Saale, Fed. Rep. Ger.), Liq. Cryst. 1991.

Dewent Abstracts: 115:124295n, "Liquid crystal composition having extended smectic C phase range and negative dielectric anisotopy", Paschke, Reinhard; Zaschke, Horst; Tschierske, Carsten; Kresse, Horst; Demus, Dietrich (Martin-Luther-Universitaet Halle-Wittenberg).

Derwent Abstracts: 115:147203v, "Preparation of thiadiazole derivative liquid crystals", Tokano, Goji; Iwaki, Takashi; Takiguchi, Takao; Yamada, Yoko; Mori, Yoshimasa (Canon K.K.), Jpn. Kokai Tokyo Koho JP 03 17,074 [91 17,074] (Cl. C07D285/12), Jan. 25, 1991, Appl. 89/152,591, Jun. 14, 1989; pp. 34 Thiadiazole derivs.

EPOXY RESINS CONTAINING THIADIAZOLE AND/OR OXADIAZOLE MOIETIES

FIELD OF THE INVENTION

The present invention pertains to epoxy resins containing more than one vicinal epoxide group per molecule and at least one thiadiazole, oxadiazole or both thiadiazole and oxadiazole moiety per molecule, curable compositions and cured compositions thereof.

BACKGROUND OF THE INVENTION

A variety of compounds containing the thiadiazole and the oxadiazole moiety have been prepared and characterized. Certain of these compounds have been shown to be mesogenic (liquid crystalline). For example, B. Linstroem, et al, *Ferroelectrics*, volume 120, number 3-4, pages 225-230 (1991) prepared a series of 2,5-(4-alkoxyphenyl)thiadiazoles and evaluated these liquid crystalline compounds for spontaneous polarization versus molecular structure. N. K. Chudgar, et al, *Mol. Cryst. Liq. Cryst.*, volume 172, pages 51-56 prepared a series of 2-amino-5[4'-(4"-n-alkoxybenzoyl)phenyl]3,4-oxadiazoles and characterized the nematic liquid crystallinity exhibited by this series of compounds. T. A. Belousova, et al, *Vysokomol. Soedin, Ser. B*, volume 33, number 5, pages 379-384 (1991) (Chemical Abstracts 115:185230j) characterized the occurrence of liquid crystallinity in fibers of poly(p-phenylene-1,3,4-oxadiazole). Epoxy resins containing the thiadiazole and/or oxadiazole moieties have heretofore not been prepared. Likewise, the class of epoxy resins wherein said thiadiazole and/or oxadiazole moieties are incorporated to form a mesogen have heretofore not been prepared.

Mesogenic epoxy resins are an emerging new class of materials taught, for example by Earls, et al. in copending applications Ser. No. 07/916,305 filed Jul. 17, 1992, Ser. No. 07/916,293 filed Jul. 17, 1992 and Ser. No. 07/919,677 filed Jul. 27, 1992. The diglycidyl ethers of 4,4'-dihydroxy-alpha-methylstilbene, 4,4'-dihydroxybenzanilide and 4'-hydroxyphenyl-4-hydroxybenzoate disclosed in the Earls, et al. applications were characterized and shown to be monotropic nematic liquid crystals. Characterization of the diglycidyl ethers of 4,4'-dihydroxy-2,2'-dimethylazoxybenzene and 4,4'-dihydroxybiphenyl revealed a lack of liquid crystallinity. Muller, et al, in U.S. Pat. No. 4,764,581 Aug. 16, 1988) characterized the diglycidyl ether of 4'-hydroxyphenyl-4-hydroxybenzoate revealing monotropic liquid crystallinity. In Hefner, Jr., et al., copending applications Ser. No. 07/905,592 filed Jun. 26, 1992 and Ser. No. 07/905,594 filed Jun. 26, 1992, the diglycidyl ester of 4,4'-stilbenedicarboxylic acid was characterized and shown to be a monotropic nematic liquid crystal. Characterization of the diglycidyl ester of 4,4'-dicarboxydiphenylazomethine revealed it to be a monotropic smectic liquid crystal, while the diglycidyl ester of 4,4'-dicarboxychalcone revealed a lack of liquid crystallinity. In Hefner, Jr., et al., copending application Ser. No. 07/890,735 filed May 28, 1992, the diglycidyl amine of N,N'-dimethyl-4,4'-diaminostilbene was characterized and shown to not be liquid crystalline. The majority of mesogenic epoxy resins which have been prepared and characterized exhibit monotropic liquid crystallinity.

Unexpectedly, certain of the mesogenic epoxy resin compositions of the present invention, notably the diglycidyl ethers of 2,5-(4-hydroxyphenyl)thiadiazole and 2,5-(4-hydroxyphenyl)oxadiazole have been shown to be enantiotropic liquid crystals, rather than monotropic liquid crystals. Copolymers prepared from mixtures containing the aforementioned diglycidyl ethers possess high glass transition temperatures concurrent with liquid crystallinity. This liquid crystalline morphology is susceptible to orientation during processing, for example as induced by shear or flow, which can result in enhanced unidirectional mechanical properties. This is not possible to any great extent with conventional epoxy resins.

SUMMARY OF THE INVENTION

One aspect of the invention concerns epoxy resins containing an average of more than one vicinal epoxide group per molecule and at least one thiadiazole, oxadiazole or both at least one thiadiazole and at least one oxadiazole moiety per molecule.

Another aspect of the present invention concerns a blend comprising (A) at least one epoxy resin containing an average of more than one vicinal epoxide group per molecule and at least one thiadiazole, oxadiazole or both at least one thiadiazole and at least one oxadiazole moiety per molecule, with (B) at least one epoxy resin containing an average of more than one vicinal epoxide group per molecule.

Another aspect of the present invention concerns the product of the advancement reaction of (A) at least one epoxy resin containing an average of more than one vicinal epoxide group per molecule and at least one thiadiazole, oxadiazole or both at least one thiadiazole and at least one oxadiazole moiety per molecule, with (B) at least one compound containing an average of more than one hydrogen atom per molecule reactive with a vicinal epoxide group; and wherein component (A) and component (B) are present in an amount which provides a mole ratio of from about 0.01 to about 0.94 epoxide reactive hydrogen atoms in component (B) to epoxide groups in component (A).

Another aspect of the present invention concerns a curable blend comprising (A) at least one epoxy resin containing an average of more than one vicinal epoxide group per molecule and at least one thiadiazole, oxadiazole or both at least onethiadiazole and at least one oxadiazole moiety per molecule, with (B) a curing amount of at least one suitable curing agent and/or curing catalyst therefor.

Another aspect of the present invention concerns a curable blend comprising (A) a blend comprising (1) at least one epoxy resin containing an average of more than one vicinal epoxide group per molecule and at least one thiadiazole, oxadiazole or both at least one thiadiazole and at least one oxadiazole moiety per molecule, with (2) at least one epoxy resin containing an average of more than one vicinal epoxide group per molecule, with (B) a curing amount of at least one suitable curing agent and/or curing catalyst therefor.

Another aspect of the present invention concerns a curable blend comprising (A) an advanced epoxy resin composition comprising the product of the advancement reaction of
  (1) at least one epoxy resin containing an average of more than one vicinal epoxide group per molecule and at least one thiadiazole, oxadiazole or both at least one thiadiazole and at least one oxadiazole moiety per molecule, with
  (2) at least one compound containing an average of more than one hydrogen atom per molecule reactive with a vicinal epoxide group, wherein component (2) and component (1) are present in an amount which provides a mole ratio of from about 0.01 to about 0.94 epoxide reactive hydrogen atoms in component (1) to epoxide groups in component (2), with
(B) a curing amount of at least one suitable curing agent and/or curing catalyst therefor.

Another aspect of the present invention concerns the product or article resulting from curing the aforementioned curable compositions.

Another aspect of the present invention concerns a phenoxy resin composition comprising the product of the advancement reaction of
(A) at least one epoxy resin containing an average of more than one vicinal epoxide group per molecule and at least one thiadiazole, oxadiazole or both at least one thiadiazole and at least one oxadiazole moiety per molecule, with
(B) at least one compound containing an average of more than one hydrogen atom per molecule reactive with a vicinal epoxide group, wherein component (A) and component (B) are present in an amount which provides a mole ratio of from about 0.95 to 1.05 epoxide reactive hydrogen atoms in component (B) to epoxide groups in component (A).

DETAILED DESCRIPTION OF THE INVENTION

Compounds Containing Thiadiazole, Oxadiazole or Both Thiadiazole and Oxadiazole Moieties Typical of the compounds containing one or more thiadiazole, oxadiazole or both thiadiazole and oxadiazole moieties used to prepare the epoxy resins which contain one or more thiadiazole, oxadiazole or both thiadiazole and oxadiazole moieties per molecule of the present invention include those represented by the Formula I $$X-Ar-(X^1)_n-N-(X^1)_n-(Ar-(X^1)_n-N-(X^1)_n)_{n^1}-Ar-X \quad \text{FORMULA I}$$

wherein each X is independently a —OH, —SH, —NHR or —COOH group; each N is independently selected from the group consisting of a

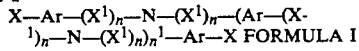

each Ar is independently selected from the group consisting of a

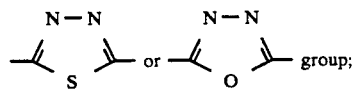

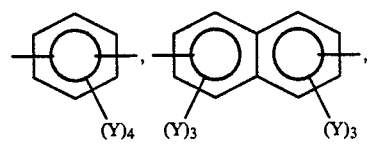
group;

each $X^1$ is independently a —O—, —S—, —SO—, —SO$_2$—, —CO—, —O—CO—, —CO—O—, —S—CO—, —CO—S—, —NR—CO—, —CO—NR—, —NR—CO—NH—, —NH—CO—NR—, —NH—CO—O— or —O—CO—NH— group; each R is independently hydrogen or a hydrocarbyl group having from one to about 10, preferably one to about 4, carbon atoms; each Y is independently —H, a hydrocarbyl or hydrocarbyloxy group having from one to about 10, preferably one to about 4, carbon atoms, a halogen atom, preferably chlorine, bromine or fluorine, a nitro group, a nitrile group, a —CO—R group or a —CO—OR group; A is a divalent hydrocarbyl group having from one to about 10, preferably from one to about 4, carbon atoms and can also contain one or more heteroatoms selected from N, O, and S; each n independently has a value of zero or one and $n^1$ has a value of zero to about 10. The term hydrocarbyl as employed herein means any aliphatic, cycloaliphatic, aromatic, aryl substituted aliphatic or cycloaliphatic or aliphatic or cycloaliphatic substituted aromatic groups. The aliphatic or cycloaliphatic groups can be saturated or unsaturated. Likewise, the term hydrocarbyloxy means a hydrocarbyl group having an oxygen linkage between it and the carbon atom to which it is attached.

Representative of the compounds containing one or more thiadiazole, oxadiazole or both thiadiazole and oxadiazole moieties include, for example, 2,5-(4-hydroxyphenyl)thiadiazole, 2,5-(4-hydroxyphenyl)oxadiazole, 2,5-(3-hydroxyphenyl)thiadiazole, 2,5-(3-hydroxyphenyl)oxadiazole, 2,5-(2-hydroxyphenyl)thiadiazole, 2,5-(2-hydroxyphenyl)oxadiazole, 2,5-(3-cyano-4-hydroxyphenyl)thiadiazole, 2,5-(3-nitro-4-hydroxyphenyl)thiadiazole, 2,5-(3-bromo-4-hydroxyphenyl)thiadiazole, 2,5-(3-methyl-4-hydroxyphenyl)thiadiazole, 2,5-(4-carboxyphenyl)thiadiazole, 2,5-(4-carboxyphenyl)oxadiazole, 2,5-(4-mercaptophenyl)thiadiazole, 2,5-(4-mercaptophenyl)oxadiazole, 2,5-(4-aminophenyl)thiadiazole, 2,5-(4-aminophenyl)oxadiazole, 2,5-(4-N-methylaminophenyl)thiadiazole, 2,5-(4-N-methylaminophenyl)oxadiazole,

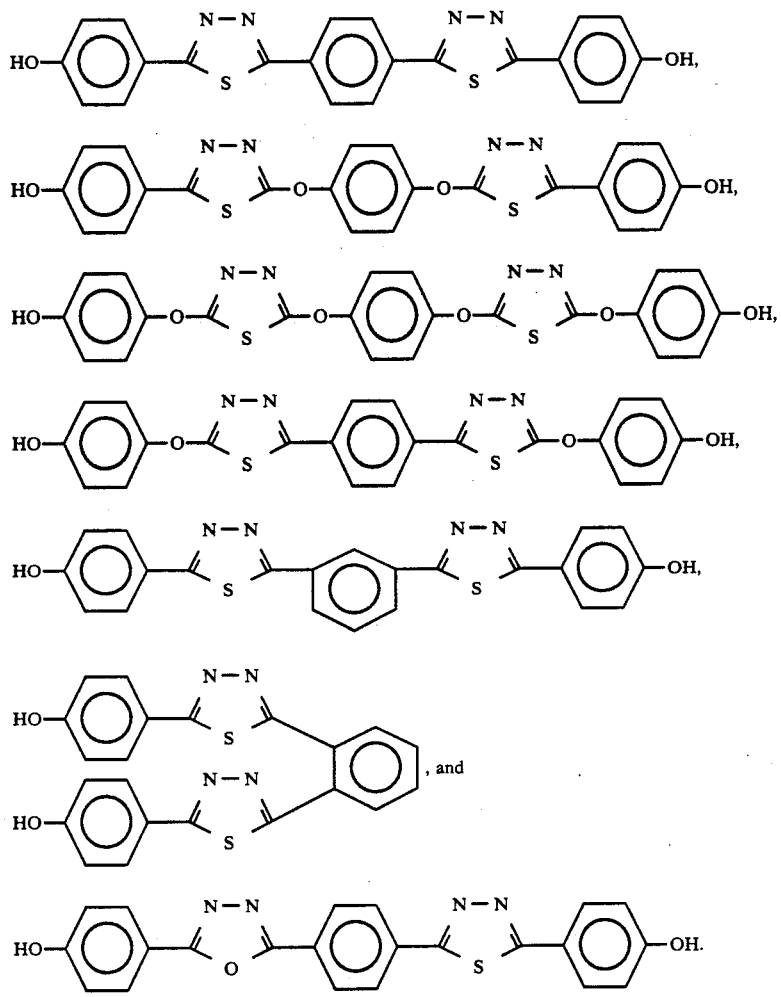

The compounds containing one or more thiadiazole, oxadiazole or both thiadiazole and oxadiazole moieties are prepared using well known methods. Thus, the substituted 2,5-diaryl-1,3,4-thiadiazoles are prepared via any of the following reactions:

(A) Treatment of substituted aromatic aldehydes with sulfur and hydrazine hydrate, typically in a 1:2:3 ratio, respectively under Willgerodt conditions from about 140° C. to about 180° C. for from about 4 to about 24 hours, preferably at 150° C. for 12 hours. Solvents such as ethanol, pyridine, dioxane, N,N-dimethylformamide are useful for conducting this reaction. This reaction proceeds through the intermediate benzalazine formed via reaction of one equivalent of hydrazine with two equivalents of the aromatic aldehyde. The benzalazine may be formed via reaction at temperatures below 150° C., for example by refluxing in one of the aforementioned solvents for from 8 to about 96, preferably about 48 hours, isolated, and then later converted to the thiadiazole compound; or (B) Treatment of thiadiazolidines with sulfur; or (C) Cyclization of 1,2-dithiobenzoylhydrazines via removal of one equivalent of hydrogen sulfide per equivalent of dithiobenzoylhydrazine; or (D) Treatment of 1,2-dibenzoylhydrazines with phosphorus pentasulfide in pyridine by heating at a temperature of from about 200° C. to about 300° C. for from about 1 to about 3 hours, preferably at 250° C. for about 2 hours.

(E) Oxidation of thiobenzoylhydrazones of aromatic aldehydes; or (F) Reaction of phenyl substituted 1-chloro-1,4-diphenyldiazabutadienes with potassium ethylxanthate in ethanol at 60° C. for one hour to provide the phenyl substituted 1,4-diphenyl-1-ethylxanthyl-2,3-diazabutadiene which is cyclized to the phenyl substituted 2,5-diphenyl-1,3,4-thiadiazole by heating at a temperature of from about 200° C. to about 260° C. for from about 8 to about 30 hours, preferably at 240° C. for 20 hours. Reaction of phenyl substituted 1-chloro-1,4-diphenyldiazabutadienes with sodium hydrosulfide in refluxing ethanol for 0.5 hour provides the phenyl substituted 2,5-diphenyl-1,3,4-thiadiazole. Reaction of phenyl substituted 1-chloro-1,4-diphenyldiazabutadienes with thiourea in refluxing dry ethanol for four hours provides the phenyl substituted 2,5-diphenyl-1,3,4-thiadiazole.

A specific synthesis of 2,5-(4-hydroxyphenyl)-thiadiazole and 2,5-(2-hydroxyphenyl)thiadiazole via the reaction of 4-hydroxybenzaldehyde or 2-hydroxybenzaldehyde, respectively, with sulfur and hydrazine monohydrate using the aforementioned Willgerodt conditions is taught by Mazzone, et al, *Journal of Heterocyclic Chemistry*, volume 20, pages 1399–1401 (1983).

Likewise, a specific synthesis of 2,5-(4-nitrophenyl)-thiadiazole from the corresponding 4-nitrobenzaldehyde precursor using the aforementioned Willergrodt conditions is taught by the aforementioned Mazzone, et al reference. The nitro groups of said thiadiazole can be reduced using conventional methods well established in the art to the corresponding amino groups to provide 2,5-(4-aminophenyl)thiadiazole. A specific synthesis of 2,5-(3-methylphenyl)thiadiazole from the corresponding 3-methylbenzaldehyde precursor using the aforementioned Willergrodt conditions is taught by the aforementioned Mazzone, et al reference. The methyl groups can be oxidized with potassium permanganate in aqueous pyridine by heating at a temperature of from about 40° C. to about 100° C. for from about 1 to about 24 hours preferably at 60° C. to 80° C. for from about 2 to about 8 hours using the method taught by Javaid and Smith, Journal of Chemical Research (S), pages 118-119 (1984) to provide 2,5-(3-carboxyphenyl)-thiadiazole.

The 2,5-diaryl substituted-1,3,4-oxadiazoles are prepared via any of the following reactions:

(A) Treatment of substituted 1,2-dibenzoylhydrazines with phosphorus oxychloride, typically at reflux for from about 3 hours to about 24 hours. Solvents such as excess phosphorus oxychloride, N-methyl-2-pyrrolidone and N-cyclohexyl-2-pyrrolidone are useful for conducting this reaction; or (B) Treatment of substituted 1,2-dibenzoylhydrazines with dehydrating agents such as thionyl chloride, polyphosphoric acid (by heating at a temperature of from about 100° C. to about 205° C. for from about 10 minutes to about 5 hours, preferably at 185° C. to 205° C. for 10 minutes) phosphorous pentoxide (by heating at a temperature of from about 200° C. to about 300° C. for from about 1 to about 3 hours, preferably at 250° C. for about 2 hours), acetic anhydride, sulfur trioxide, or methanesulfonic acid and phosphorous pentoxide mixture; or (C) Cyclization of disilyldiacyldiarylhydrazines in the presence of basic, acidic, neutral (transition metals on inert supports) or free radical initiators as catalysts, using the methods of Rigo, et al, Synthetic Communications, volume 19, pages 2321-2335 (1989). As a specific example of these methods, addition of a bis-trimethylsilyldiacylhydrazine to trifluoromethane sulfonic acid catalyst (11 percent) under a nitrogen atmosphere, followed by heating at 75° C. for 3 hours then evaporation to remove hexamethyldisiloxane produced a quantitative yield of cyclized product.

A specific synthesis of 2,5-[4-(3-aminophenoxy)]-1,3,4-oxadiazole via the reaction of 2,5-(4-fluorophenyl)thiadiazole with 3-aminophenol, using N-methyl-2-pyrrolidone and N-cyclohexyl-2-pyrrolidone solvents in the presence of potassium carbonate is taught by Hedrick, Polymer Preprints, volume 33, number 1, pages 1016-1017 (April, 1992). The reaction is initially conducted at 150° C. with removal of water from the phenoxide formed, followed by displacement reaction at 185° C. for twenty hours. A specific synthesis of 2,5-(carboxylphenyl)oxadiazoles via oxidization of the methyl groups of the 2,5-(methylphenyl)oxadiazole precursor with potassium permanganate in aqueous pyridine by heating at a temperature of from about 40° C. to about 100° C. for from about 1 to about 24 hours, preferably at 60° C. to 80° C. for from about 2 to about 8 hours, is taught by Javaid and Smith, Journal of Chemical Research (S), pages 118-119 (1984).

Epoxy Resins Containing Thiadiazole, Oxadiaxole or Both Thiadiazole and Oxadiazole Moieties Typical of the epoxy resins containing one or more thiadiazole, oxadiazole or both thiadiazole and oxadiazole moieties of the present invention are those represented by the following Formula II:

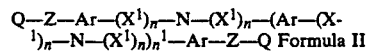

wherein each Z is independently a —O—, —S—, —NR—, —N< or —COO— group; Q is

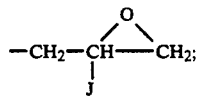

J is hydrogen or a hydrocarbyl group having from one to about 4, preferably one, carbon atom(s); each N is independently a

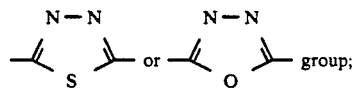

each Ar is independently a

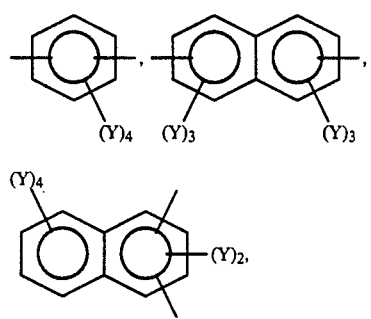

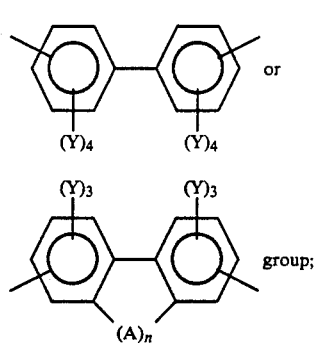

each $X^1$ is independently a —O—, —S—, —SO—, —SO$_2$—, —CO—, —O—CO—, —CO—O—, —S—CO—, —CO—S—, —NR—CO—, —CO—NR—, —N-R—CO—NH—, —NH—CO—NR—, —NH—CO—O— or —O—CO—NH— group; each R is independently hydrogen or a hydrocarbyl group having from one to about 10, preferably from one to about 4, carbon atoms; each Y is independently hydrogen, a hydrocarbyl or hydrocarbyloxy group having from one to about 10, preferably from one to about 4, carbon atoms, a halogen atom, preferably chlorine, bromine or fluorine, a nitro group, a nitrile group, a —CO—R group or a —CO—OR group; A is a divalent hydrocarbyl group having from one to about 10, preferably from one to about 4, carbon atoms and can also contain one or more heteroatoms selected from N, O, and S; each n independently has a value of zero or one and n¹ has a value of zero to about 10.

The term hydrocarbyl as employed herein means any aliphatic, cycloaliphatic, aromatic, aryl substituted aliphatic or aryl substituted cycloaliphatic or aliphatic substituted or cycloaliphatic substituted aromatic groups. The aliphatic or cycloaliphatic groups can be saturated or unsaturated. Likewise, the term hydrocarbyloxy means a hydrocarbyl group having an oxygen linkage between it and the carbon atom to which it is attached.

Certain of the epoxy resins are mesogenic, for example, those represented by the aforementioned Formula II wherein at least about 80 percent of the molecules are para substituted by the N and Q—Z— groups and the X¹ groups which are present when n has a value of one, X¹ when present is selected from the group consisting of —O—CO—, —CO—O—, —S—CO—, —CO—S—, —NR—CO—, —CO—NR—, and each Ar is independently selected from the group consisting of

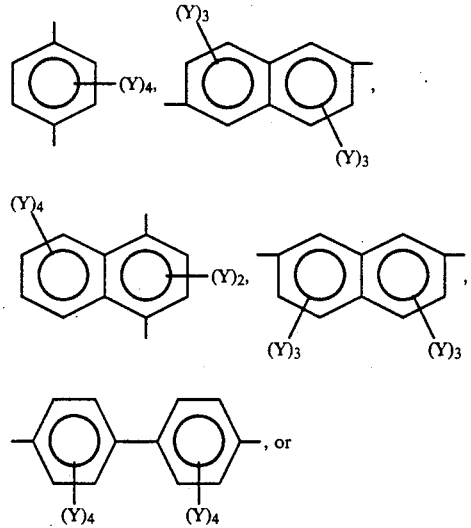

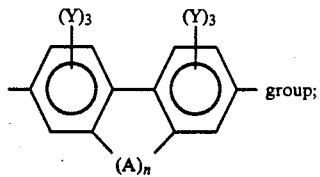

wherein each Y is independently hydrogen or a methyl group, with the proviso that no more than one Y group per aromatic ring is a methyl group.

The term "mesogenic" or "mesogen" as is used herein designates compounds containing one or more rigid rodlike structural units which have been found to favor the formation of liquid crystal phases in the case of low molar mass substances. Thus the mesogen or mesogenic moiety is that structure responsible for molecular ordering. The term mesogenic is further defined by R. A. Weiss (ed.) and C. K. Ober (ed.) in *Liquid-Crystalline Polymers*, ACS Symposium Series 435 (1989) on page 2: "The rigid unit responsible for the liquid crystalline behavior is referred to as the mesogen," and "Liquid crystalline order is a consequence solely of molecular shape anisotropy, such as found in rigid rod-shaped molecules . . . ". Further definition of the term mesogenic may be found in *Polymeric Liquid Crystals*, Alexandre Blumstein (ed.), (1983) on pages 2–3 and in *Polymeric Liquid Crystals*, A. Ciferri, W. R. Krigbaum and Robert B. Meyer (eds.) (1982) on pages 5–9, both of which are incorporated herein by reference.

Representative of the epoxy resins containing one or more thiadiazole, oxadiazole or both thiadiazole and oxadiazole moieties include, for example, the diglycidyl ethers of: 2,5-(4-hydroxyphenyl)thiadiazole, 2,5-(4-hydroxyphenyl)oxadiazole, 2,5-(3-hydroxyphenyl)thiadiazole, 2,5-(3-hydroxyphenyl)oxadiazole, 2,5-(2-hydroxyphenyl)thiadiazole, 2,5-(2-hydroxyphenyl)oxadiazole, 2,5-(3-cyano-4-hydroxyphenyl)thiadiazole, 2,5-(3-nitro-4-hydroxyphenyl)thiadiazole, 2,5-(3-bromo-4-hydroxyphenyl)thiadiazole, 2,5-(3-methyl-4-hydroxyphenyl)thiadiazole,

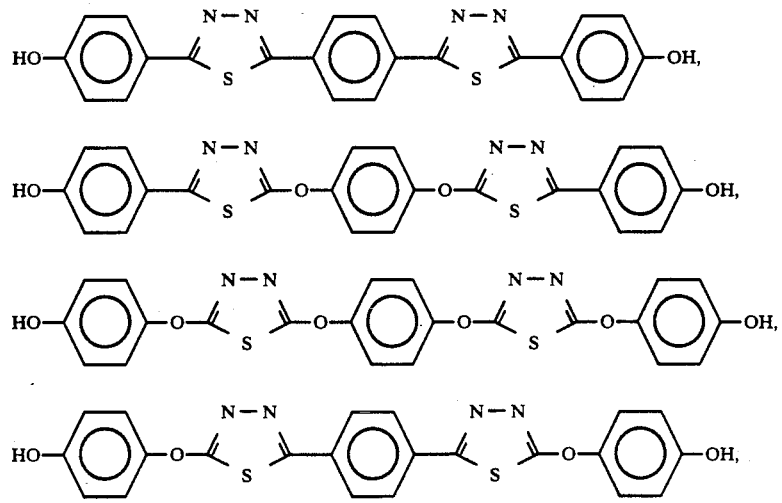

-continued

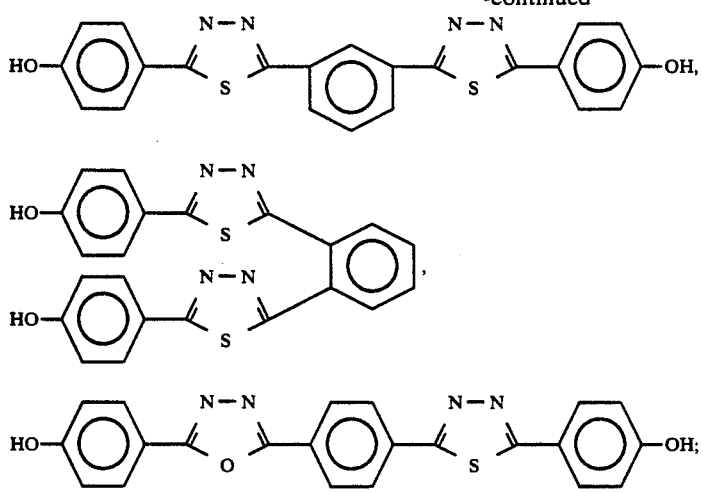

the diglycidyl esters of: 2,5-(4-carboxyphenyl)-thiadiazole and 2,5-(4-carboxyphenyl)oxadiazole; the diglycidyl thioethers of: 2,5-(4-mercaptophenyl)-thiadiazole and 2,5-(4-mercaptophenyl)oxadiazole; the diglycidyl amines of: 2,5-(4-aminophenyl)thiadiazole, 2,5-(4-aminophenyl)oxadiazole, 2,5-(4-N-methylaminophenyl)thiadiazole and 2,5-(4-N-methylaminophenyl)oxadiazole. Especially preferred epoxy resin compositions are the diglycidyl ethers of: 2,5-(4-hydroxyphenyl)thiadiazole and 2,5-(4-hydroxyphenyl)oxadiazole because of their mesogenic character.

Epoxidation of the diphenol, dicarboxylic acid, dithiophenol and diamino compounds used to prepare the epoxy resins containing one or more thiadiazole, oxadiazole or both thiadiazole and oxadiazole moieties of the present invention can be performed by the known methods described in *Handbook of Epoxy Resins* by Lee and Neville, McGraw-Hill, 1967; Japan Kokai Tokkyo Koho JP 62 86,484 (87 96,484); EP 88-008358/92 and *Journal of Applied Polymer Science*, volume 23, pages 1355–1372 (1972) all of which are incorporated herein by reference. This usually includes reacting the respective diphenol (dicarboxylic acid, dithiophenol or diamino compound) with an excess of an epihalohydrin such as, for example, epichlorohydrin, methyl epichlorohydrin or epibromohydrin, at a temperature of from about 0° C. to about 100° C., preferably from about 20° C. to about 65° C. followed by dehydrohalogenation with a basic-acting material such as, for example, an alkali metal hydroxide, typically sodium hydroxide, at a temperature of from about 0° C. to about 100° C., preferably from about 20° C. to about 65° C. and finally recovering the resulting glycidyl ether (ester, thioether or amine) product. A prefered method for the production of the epoxy resins of the present invention is the use of an anhydrous epoxidation technique. This technique employs azeotropic removal of water/epichlorohydrin concurrent with the controlled addition of the aqueous sodium hydroxide to a reaction mixture consisting of epichlorohydrin, a diphenol (dicarboxylic acid, dithiophenol, diamine), a phase transfer catalyst such as, for example, benzyltrimethylammonium chloride or tetra-n-butylammonium bromide, and, optionally, solvent(s). It is advantageous to conduct such anhydrous epoxidation reactions under a vacuum to facilitate the azeotropic removal of water. The azeotropic removal of water is usually conducted at temperatures of from about 20° C. to about 100° C., preferably from about 30° C. to about 65° C. It is also operable and advantageous to utilize sodium hydroxide free of water as the alkali metal hydroxide reactant. In order to control reaction exotherm, the solid sodium hydroxide is typically added in aliquots as a powder to the epoxidation reaction mixture. A typical anhydrous epoxidation technique is described by Wang, et al. in U.S. Pat. No. 4,499,255 which is incorporated herein by reference in its entirety.

Another specific anhydrous epoxidation technique involves catalytic coupling of the diphenol (dicarboxylic acid, dithiophenol, diamine) compound with an epihalohydrin, typically using as a catalyst one or more of the quaternary ammonium halides. The resultant solution of halohydrin in excess epihalohydrin is then treated with finely pulverized potassium carbonate to effect the dehydrohalogenation to the epoxy resin.

Advanced Epoxy Resins Containing Thiadiazole, Oxadiazole or Both Thiadiazole and Oxadiazole Moieties Advancement reaction of the epoxy resins containing one or more thiadiazole, oxadiazole or both thiadiazole and oxadiazole moieties with one or more compounds having an average of more than one active hydrogen atom per molecule can be performed by the known methods described in the aforementioned *Handbook of Epoxy Resins*. This usually includes combining the compound(s) having an average of more than one hydrogen atom reactive with an epoxide group per molecule and the epoxy resin(s) with the application of heat and mixing to effect the advancement reaction. A catalyst is frequently added to facilitate the advancement reaction.

The epoxy resin(s) and the compound(s) having an average of more than one hydrogen atom reactive with an epoxide group per molecule are reacted in amounts which provide suitably from about 0.001:1 to about 0.94:1, more suitably from about 0.05:1 to about 0.8:1, most suitably from about 0.1:1 to about 0.5:1 equivalents of active hydrogen atoms per equivalent of epoxide group.

Suitable compounds having an average of more than one hydrogen atom reactive with an epoxide group per molecule which can be employed to prepare the advanced epoxy resin compositions of the present invention include, for example, diphenols, dicarboxylic acids, thiodiphenols, compounds containing one primary amine group, compounds containing one primary or secondary amide group and one primary or secondary amine group, compounds containing two secondary amine groups, compounds containing one primary or secondary amine group and one —SO$_2$—NH$_2$ group, compounds containing one phenolic hydroxyl group and one carboxylic acid group, compounds containing one phenolic hydroxyl group and one primary or secondary amine group, compounds containing one carboxylic acid group and one primary or secondary amine group, or any combination thereof and the like.

Especially preferred as the compound having an average of more than one hydrogen atom reactive with an epoxide group per molecule are the compounds which contain one or more thiadiazole, oxadiazole or both thiadiazole and oxadiazole moieties represented by Formula I. Additional compounds having an average of more than one hydrogen atom reactive with an epoxide group per molecule include diphenols, such as, for example, hydroquinone, resorcinol, 4,4'-isopropylidenediphenol (bisphenol A), 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',3,5'-tetrachloro-4,4'-isopropylidenediphenol, 3,3',3,5'-tetrabromo-4,4'-isopropylidenediphenol, 3,3'-dimethoxy-4,4'-isopropylidenediphenol, 4,4'-dihydroxybiphenyl, 4,4'-dihydroxy-alpha-methylstilbene, 4,4'-dihydroxybenzanilide, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine; dicarboxylic acids, such as, for example, terephthalic acid, isophthalic acid, 4,4'-benzanilidedicarboxylic acid, 4,4'-phenylbenzoatedicarbocylic acid, 4,4'-stilbenedicarboxylic acid, adipic acid; thiodiphenols, such as, for example, 4,4'-dithiodiphenylmethane, 4,4'-isopropylidenedithiophenol, 4,4'-dithio-alphamethylstilbene; compounds containing one primary amine group, such as, for example, aniline, 4-methoxyaniline, 4-aminobiphenyl, 4-amino-N-methylbenzanilide, 4-amino-1-phenylbenzoate, phenyl-4-aminobenzoate, biphenyl-4-aminobenzoate, 1-phenyl-4'-aminophenylterephthalate; compounds containing one primary or secondary amide group and one primary or secondary amine group, such as, for example 4-aminobenzamide, 4-N-methylaminobenzamide, 4-amino-N-methylbenzamide, 4-N-methylamino-N-methylbenzamide; compounds containing two secondary amine groups, such as, for example, 4,4'-(N,N'-methylamino)diphenylmethane, 4,4'-(N,N'-methylamino)biphenyl; compounds containing one primary or secondary amine group and one —SO$_2$—NH$_2$ group, such as, for example, sulfanilamide, 4-amino-4'-sulfonamidobiphenyl, 4-N-methylamino-4'-sulfonamidobiphenyl; compounds containing one phenolic hydroxyl group and one carboxylic acid group, such as, for example, 4-hydroxybenzoic acid, 4-hydroxy-4-carboxybiphenyl; compounds containing one phenolic hydroxyl group and one primary or secondary amine group, such as, for example, 4-aminophenol, 4-N-methylaminophenol, 4-amino-4-hydroxybiphenyl and compounds containing one carboxylic acid group and one primary or secondary amine group, such as, for example, 4-aminobenzoic acid, 4-N-methylaminobenzoic acid, 4-amino-4-carboxybiphenyl.

The advancement reaction can be conducted in the presence of a suitable advancement catalyst such as, for example, phosphines, quaternary ammonium compounds, phosphonium compounds, tertiary amines, and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate.acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate.acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, tetra-n-butylammonium chloride, tetra-n-butylammonium bromide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends upon the particular reactants and catalyst employed, as well as the advancement reaction conditions to be used, however, it is usually employed in quantities of from about 0.03 to about 3, preferably from about 0.03 to about 1.5, most preferably from about 0.05 to 1.5 percent by weight based upon the weight of the epoxy-containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, xylene, methylethyl ketone, methylisobutyl ketone, diethylene glycol methyl ether, dipropylene glycol methyl ether, dimethylformamide, dimethylsulfoxide, N-methylpyrrolidinone, tetrahydrofuran, dioxane, propylene glycol methyl ether, combinations thereof and the like. The solvents can be employed in amounts from about zero to about 95%, preferably from about 20% to about 60%, more preferably from about 30% to about 50% by weight of the reaction mixture.

The advancement of the epoxy resins containing one or more thiadiazole, oxadiazole or both thiadiazole and oxadiazole moieties with one or more compounds having an average of more than one active hydrogen atom per molecule is employed to chain extend and/or branch the resin. This chain extension and/or branching is required for some of the mesogen containing resin compositions in order to obtain liquid crystal character. The advancement of the of the epoxy resins containing one or more thiadiazole, oxadiazole or both thiadiazole and oxadiazole moieties can also be used to modify the temperature range in which a particular mesogen-containing resin is liquid crystalline and to control the degree of crosslinking during the final curing. An especially preferred mesogenic advanced epoxy resin composition of the present invention results from the advancement reaction of one of the aforementioned mesogenic epoxy resins containing one or more thiadiazole, oxadiazole or both thiadiazole and oxadiazole moieties with one or more mesogenic compounds represented by the aforementioned Formula I wherein at least about 80 percent of the molecules are para substituted by the N and X groups and the $X^1$ groups which are present when n has a value of one, $X^1$ when present is —O—CO—, —CO—O—, —S—CO—, —CO—S—, —NR—CO—, or —CO—NR—, each Ar is independently a

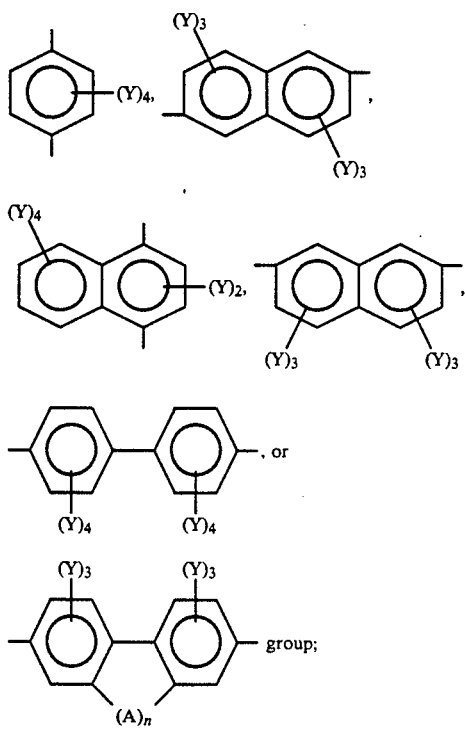

wherein each Y is independently a hydrogen atom or a methyl group with the proviso that no more than one Y group per aromatic ring is a methyl group, and X is —OH, —NHR or —COOH, with the proviso that when X is —NHR, each R is independently a hydrocarbyl group having from one to about 10, preferably one to about 4, carbon atoms.

Phenoxy Resins Containing Thiadiazole, Oxadiazole or Both Thiadiazole and Oxadiazole Moieties When the epoxy resin containing one or more thiadiazole, oxadiazole or both thiadiazole and oxadiazole moieties and the compound having an average of more than one active hydrogen atom per molecule are reacted in advancement reaction using amounts which provide suitably from about 0.95:1 to about 1.05:1 equivalents of active hydrogen atoms per equivalent of epoxide group, a relatively high molecular weight thermoplastic resinous product (sometimes referred to as a phenoxy resin) is produced. If desired, the reaction can be conducted in the presence of a suitable catalyst such as, for example, those catalysts described herein for use in the advancement reaction. These thermoplastic resin compositions contain little, if any, curable residual epoxide functionality and may even contain an active hydrogen functionality, depending upon which component is employed in excess, the epoxy resin, or the active hydrogen containing compound. When the compound having an average of more than one active hydrogen atom per molecule used in the advancement reaction is a diphenol, the resultant resinous product is a phenoxy resin. These phenoxy resins may thus be processed using the typical processing methods employed with conventional thermoplastic resins, such as, for example, injection molding or extrusion. Thermosetting may, however, be induced, for example, via reaction of all or a part of the backbone secondary aliphatic hydroxyl groups produced in the aforesaid advancement reaction, with a curing agent therefore. One class of suitable curing agents includes, for example, the di or polyisocyanates, as well as the blocked di or polyisocyanates which can be induced to react with the secondary hydroxyl groups providing urethane crosslinks between the resin chains. An example of a diisocyanate especially useful herein is 4,4'-diisocyanatodiphenyl methane.

According to the teachings found in *Encyclopedia of Polymer Science and Engineering*, volume 6, page 331, published by John Wiley and Sons, New York, N.Y. (1986), which is incorporated herein by reference, aside from the aforementioned advancement method, a phenoxy resin may also be prepared by reaction of a 1:1 mole ratio of high purity bisphenol A and epichlorohydrin. It is therefore operable to prepare the phenoxy resins of the present invention via reaction of one or more diphenols with one or more epihalohydrins. A typical material would thus be the phenoxy resin produced from the reaction of epichlorohydrin and 2,5-(4-hydroxyphenyl)thiadiazole using the aforementioned stoichiometric ratio. The reaction of the epihalohydrin and the bisphenol is usually conducted at a temperature of from about 0° C. to about 100° C., preferably from about 20° C. to about 80° C., more preferably from about 20° C. to about 65° C. for a time sufficient to complete the reaction, usually from about one to about 12, preferably from about one to about 5, more preferably from about one to about 3 hours.

An especially preferred mesogenic phenoxy resin composition of the present invention results from the advancement reaction of one of the aforementioned mesogenic epoxy resins containing one or more thiadiazole, oxadiazole or both thiadiazole and oxadiazole moieties with one or more mesogenic compounds represented by the aforementioned Formula I wherein at least about 80 percent of the molecules are para substituted by the N and X groups and the $X^1$ groups which are present when n has a value of one, $X^1$ when present is a —O—CO—, —CO—O—, —S—CO—, —CO—S—, —NR—CO—, or —CO—NR— group, each Ar is independently a

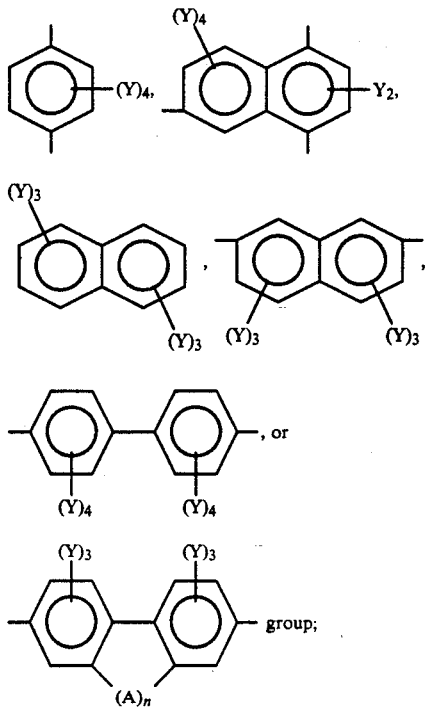

wherein each Y is independently a hydrogen atom or a methyl group with the proviso that no more than one Y group per aromatic ring is a methyl group; X is —OH, —SH, —NHR, or —COOH, with the proviso that when X is —NHR, each R is independently a hydrocarbyl group having from one to about 10, preferably one to about 4, carbon atoms.

Curing Agents and Curing Catalysts

The epoxy resins containing one or more thiadiazole, oxadiazole or both thiadiazole and oxadiazole moieties of the present invention can be cured with with any suitable curing agent or catalyst for curing epoxy resins, such as, for example, aliphatic, cycloaliphatic, polycycloaliphatic or aromatic primary monoamines; aliphatic, cycloaliphatic, polycycloaliphatic or aromatic primary and secondary polyamines; carboxylic acids and anhydrides thereof; aromatic hydroxyl containing compounds; imidazoles; guanidines; urea-aldehyde resins; melamine-aldehyde resins; alkoxylated urea-aldehyde resins; alkoxylated melamine-aldehyde resins; combinations thereof and the like. Particularly suitable curing agents include, for example, methylenedianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylamine, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like. Particularly suitable curing catalysts include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, or any combination thereof and the like.

Especially preferred as curing agents for the mesogenic epoxy resin composition and mesogenic advanced epoxy resin compositions of the present invention are one or more mesogenic compounds represented by the aforementioned Formula I wherein at least about 80 percent of the molecules are para substituted by the N and X groups and the $X^1$ groups which are present when n has a value of one, $X^1$ when present is a —O—, —CO—, —CO—O—, —S—CO—, —CO—S—, —N-R—CO—, or —CO—NR groups; each Ar is independently

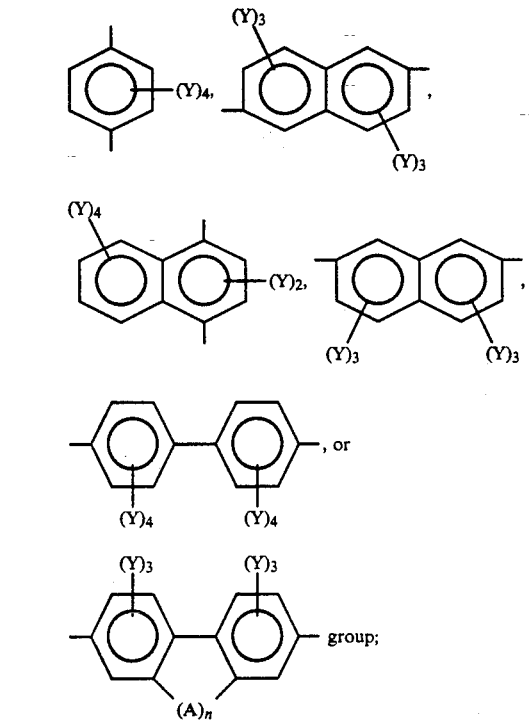

wherein each Y is independently a —H or —CH$_3$ group with the proviso that no more than one Y group per aromatic ring is —CH$_3$ and X and R are as hereinbefore defined.

The curing agents are generally employed in amounts which will effectively cure the epoxy resin, however, these amounts will depend upon the particular epoxy resin employed and curing agent employed. Generally suitable amounts include, for example, 0.80:1 to about 1.20:1 equivalents of curing agent per equivalent of epoxy resin.

The curing catalysts are employed in amounts which will effectively cure the composition, however, these amounts will depend upon the particular epoxy resin employed and curing agent employed. Generally suitable amounts include, for example, 0.001 to about 2 percent by weight of the total epoxy resin used. It is frequently of benefit to employ one or more of the curing catalysts in conjunction with one or more curing agents in the curing of the epoxy resins of the present invention. This is generally done to accelerate or otherwise modify the curing behavior obtained when a curing agent or a curing catalyst are used singly.

The curing of the curable compositions of the present invention can be conducted at atmospheric, superatmospheric or subatmospheric pressures at temperatures of from about 0° C. to about 300° C., preferably from about 50° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about one minute to about 48 hours, preferably from about 15 minutes to about 8 hours, more preferably from about 30 minutes to about 3 hours are suitable.

For the curable blends of epoxy resins and/or advanced epoxy resins of the present invention with one or more curing agents, when mesogenic moieties are present in one or more components of said blends, it is frequently of value to B-stage the curable blend in order to chain extend the resin. This chain extension is required for some mesogen containing epoxy resin compositions in order to achieve liquid crystal character. B-staging can also be employed to increase the temperature range at which a particular resin composition is liquid crystalline and to control the degree of crosslinking during the final curing stage.

For the curable blends of epoxy resins and/or advanced epoxy resins of the present invention with one or more curing agents, when mesogenic moieties are present in one or more components of said blends, before and/or during processing and/or curing into a part, electric or magnetic fields, drawing and/or shear stresses can be applied for the purpose of orienting the liquid crystal moieties contained or developed therein which in effect improves the mechanical properties. As specific examples of these methods, Finkelmann, et al, *Macromol. Chem.*, volume 180, pages 803–806 (March, 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Kruecke, *Macromol. Chem.*, volume 187, pages 2655–2662 (November, 1986). Magnetic field induced orientation of mesogenic main chain containing polymers has been demonstrated by Moore, et al, *ACS Polymeric Materials Science and Engineering*, volume 52, pages 84–86 (April-May, 1985). Magnetic and electric field orientation of low molecular weight mesogenic compounds is discussed by W. R. Krigbaum in *Polymer Liquid Crystals*, pages 275–309 (1982) published by Academic Press, Inc. All of the above are incorporated herein by reference in their entirety.

In addition to orientation by electric or magnetic fields, polymeric mesophases can be oriented by shear forces which are induced by drawing and/or flow through dies, orefices and mold gates. A general discussion for orientation of thermotropic liquid crystal polymers by this method is given by S. K. Garg and S. Kenig in *High Modulus Polymers*, pages 71–103 (1988) published by Marcel Dekker, Inc. For the mesomorphic systems based on the epoxy and phenoxy resin compositions, this shear orientation can be produced by processing methods such as injection molding, extrusion, pultrusion, filament winding, filming and prepreging.

Other Epoxy Resins

The epoxy resins containing one or more thiadiazole, oxadiazole or both thiadiazole and oxadiazole moieties can also be combined with one or more epoxy resins free of thiadiazole and/or oxadiazole moieties. Generally, suitable amounts of the epoxy resins containing one or more thiadiazole, oxadiazole or both thiadiazole and oxadiazole moieties are from about 1 to about 99, more suitably from about 10 to about 80, most suitably from about 10 to about 50 weight percent based on the total weight of the combined resins. Curable mixtures may be formed via addition of one or more of the aforementioned curing agents and/or curing catalysts.

Suitable epoxy resins which can be combined with the epoxy resins containing one or more thiadiazole, oxadiazole or both thiadiazole and oxadiazole moieties include any compound containing an average of more than one vicinal epoxide group per molecule and no thiadiazole and/or oxadiazole moieties. Suitable such epoxy resins include, for example, aromatic di and/or polyepoxides, aliphatic di and/or polyepoxides, cycloaliphatic or polycycloaliphatic di and/or polyepoxides, or any combination thereof and the like. Particularly suitable epoxy resins include the diglycidyl ethers of (a) compounds containing one or more aromatic rings and two or more aromatic hydroxyl groups per molecule; (b) compounds which are the result of reacting an alkylene oxide or monoglycidyl ether compound with the compounds of (a); (c) aliphatic diols which contain ether oxygen atoms or which are free of ether oxygen atoms; (d) cycloaliphatic or polycycloaliphatic compounds containing more than one hydroxyl group per molecule.

Particularly suitable epoxy resins include, for example, (a) the diglycidyl ethers of: resorcinol, hydroquinone, 4,4'-isopropylidenediphenol (bisphenol A), 4,4'-dihydroxydiphenylmethane (bisphenol F), 4,4'-dihydroxybenzophenone, 3,3'5,5'-tetrabromo-4,4'-isopropylidenediphenol, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachloro-4,4'-isopropylidenediphenol A, 3,3'-dimethoxy-4,4'-isopropylidenediphenol, 4,4'-dihydroxy-alpha-methylstilbene, 4,4'-dihydroxybenzanilide, 4,4'-dihydroxyazoxybenzene, 4,4'-dihydroxybiphenyl; (b) the triglycidyl ether of tris(hydroxyphenyl)methane; (c) the polyglycidyl ethers of a phenol or alkyl or halogen substituted phenolaldehyde acid catalyzed condensation product (novolac resins); the polyglycidyl ether of the condensation product of a dicyclopentadiene or an oligomer thereof and a phenol or alkyl or halogen substituted phenol; (d) the advancement reaction products of the aforesaid di and polyglycidyl ethers with aromatic di and polyhydroxyl or carboxylic acid containing compounds including, for example hydroquinone, resorcinol, catechol, 2,4-dimethylresorcinol, 4-chlororesorcinol, tetramethylhydroquinone, 4,4'-isopropylidenediphenol (bisphenol A), 4,4'-dihydroxydiphenylmethane, 4,4'-thiodiphenol, 4,4'-sulfonyldiphenol, 2,2'-sulfonyldiphenol, 4,4'-dihydroxydiphenyl oxide, 4,4'-dihydroxybenzophenone, 1,1-bis(4-hydroxyphenyl)-1-phenylethane, 4,4'-bis(4(4-hydroxyphenoxy)phenylsulfone)-diphenyl ether, 4,4'-dihydroxydiphenyl disulfide, 3,3',5,5'-tetrachloro-4,4'-isopropylidenediphenol, 3,3',5,5'-tetrabromo-4,4'-isopropylidenediphenol, 3,3'-dimethoxy-4,4'-isopropylidenediphenol, 4,4'-dihydroxybiphenyl, 4,4'-dihydroxy-alpha-methylstilbene, 4,4'- dihydroxybenzanilide, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine; 1,1'-bis(4-hydroxyphenyl)cyclohexane, phloroglucinol, pyrogallol, 2,2',5,5'-tetrahydroxydiphenyl sulfone, tris(hydroxyphenyl)methane, dicyclopentadiene diphenol, tricyclopentadiene diphenol, terephthalic acid, isophthalic acid, 4,4'-benzanilidedicarboxylic acid, 4,4'-phenylbenzoatedicarboxylic acid, 4,4'-stilbenedicarboxylic acid, adipic acid; and (e) any combination of the aforementioned epoxy resins and the like.

Other Components

The epoxy resins containing one or more thiadiazole, oxadiazole or both thiadiazole and oxadiazole moieties or such epoxy resins in combination with other epoxy resins can be blended with other materials such as solvents or diluents fillers, pigments, dyes, flow modifiers, thickeners, reinforcing agents, mold release agents, wetting agents, stabilizers, fire retardant agents, surfactants, or any combination thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended compositions.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, xylene, methylethylketone, methylisobutylketone, diethylene glycol methyl ether, dipropylene glycol methyl ether, dimethylformamide, N-methylpyrrolidinone, tetrahydrofuran, dioxane, propylene glycol methyl ether, combinations thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, calcium carbonate, combinations thereof and the like.

The fillers can be employed in amounts suitably from about zero to about 95, more suitably from about 10 to about 80, most suitably from about 40 to about 60 percent by weight based upon the weight of the total composition.

The epoxy resins containing one or more thiazole or oxazole or both thiazole and oxazole moieties of the present invention can be employed in such applications as coating, casting, encapsulation, electronic or structural laminate or composite, filament winding, molding, and the like.

The following examples are illustrative of the present invention, but are not to be construed as to limiting its scope in any manner.

EXAMPLE 1

A. Synthesis of 2,5-(4-hydroxyphenyl)thiadiazole p-Hydroxybenzaldehyde (50.0 grams, 0.409 mole), sulfur (26.27 grams, 0.819 mole), and ethylene glycol (250 milliliters) are added to a one liter glass reactor equipped with a condenser venting through a scrubber charged with aqueous sodium hydroxide solution, stirring, a nitrogen inlet flowing at a rate of one liter per minute, an addition funnel and a thermometer-heating mantle-temperature controller assembly. Hydrazine monohydrate (65.02 grams, 1.299 mole) and additional ethylene glycol (150 milliliters) are added dropwise to the reactor inducing an exotherm to 35° C. After completion of the addition, heating to 100° C. commences over the next 1.5 hours. After 16 hours at the 100° C. temperature, a slurry of crystals are observed in the reactor and are recovered via filtration. The recovered crystals are transferred to a 316 stainless steel one liter Parr reactor along with additional sulfur (12.5 grams, 0.39 mole) and ethylene glycol (400 milliters). The Parr reactor is sealed, purged with nitrogen, then stirring and heating to 140° C. commence. Once the reactor has stabilized at the 140° C. temperature, gradual heating to 160° C. commences and this temperature is maintained for the next 16 hours. The reactor is cooled to room temperature (24° C.) and the resultant crystalline slurry product is recovered and filtered. The recovered crystals are added to a two liter beaker along with ethanol (1800 milliliters) then boiled with stirring to provide a hazy solution. Filtration of the hot, hazy solution is completed and the resulting clear filtrate is cooled to room temperature. After four hours at room temperature, the crystals formed in the filtrate are recovered by filtration then dried under vacuum at 100° C. and 1 mm Hg to a constant weight of 30.6 grams. A second crop of crystals (0.81 gram) are recovered by rotary evaporation of the filtrate to a volume of 400 milliliters followed by cooling to room temperature, filtration and drying under vacuum. Fourier transform infrared spectrophotometric analysis of a potassium bromide pellet of the product reveals the presence of absorptions at 1609, 1583, 1523, 1443 and 1384 cm$^{-1}$ characteristic of the aromatic ring and the thiadiazole ring, the hydroxyl group O—H stretching centered at 3336 cm$^{-1}$ and the out-of-plane C—H bending vibration at 839 cm$^{-1}$ indicative of para-disubstitution. Differential scanning calorimetry of a portion of the product (14.8 milligrams) heated at 10° C. per minute under nitrogen flowing at 35 cubic centimeters per minute reveals a sharp melting point endotherm (128.0 joules per gram) with a minimum at 333.2° C. Proton magnetic resonance spectroscopy and $^{13}$carbon magnetic resonance spectroscopy further substantiated the product structure. High pressure liquid chromatographic analysis using an ultraviolet absorbance detector reveals a single peak comprising 85.7 area % (molar absorptivity not determined) of the product, with the balance of the area contained in a pair of minor coproduct peaks.

B. Epoxidation of 2,5-(4-hydroxyphenyl)thiadiazole 2,5-(4-Hydroxyphenyl)thiadiazole (13.51 grams, 0.10 hydroxyl equivalent) from A above, epichlorohydrin (462.7 grams, 5.0 moles) and tetrabutylammonium bromide (0.135 gram, 1.00% wt. of the diphenol reactant used) are added to a one liter glass round bottom reactor and heated to 75° C. with magnetically driven stirring under a nitrogen atmosphere flowing at a rate of one liter per minute. The bright yellow colored reactant slurry becomes a clear solution after 501 minutes at the 75° C. reaction temperature. After 741 minutes at 75° C., high pressure liquid chromatographic analysis of a portion of the light amber colored solution demonstrates that complete conversion of the diphenol has occurred. At this time, a water separator is interspersed between the reactor and the chilled (−2.5° C.) glycol condenser and an addition funnel containing sodium hydroxide (4.5 grams, 0.1125 mole) dissolved in deionized water (5.5 grams, 55% wt. of the solution) and a vacuum line are added to the reactor. The nitrogen purge is shut off simultaneous with initiation of the vacuum. The vacuum and reaction temperature are equilibrated at 69 mm Hg and 50° C., respectively and such that a vigorous reflux is maintained with continuous return of dry epichlorohydrin from the water separator to the reactor. After equilibration, dropwise addition of the aqueous sodium hydroxide commences. After 50 minutes, addition of the aqueous sodium hydroxide is complete. After an additional 2.5 hours at the 69 mm Hg vacuum and 50° C. reaction temperature, heating ceases, vacuum is released and the product slurry recovered. The recovered slurry is filtered through a bed of diatomaceous earth while still hot and the resultant light amber colored solution rotary evaporated under a vacuum with heating to 90° C. After removal of about 50% of the epichlorohydrin volume, the product became a crystalline slurry. Rotary evaporation is continued until about 75% of the epichlorohydrin volume is removed. The resultant slurry is allowed to cool to room temperature (23° C.), then filtered after four hours at room temperature. After filtration the crystalline product is extracted with acetone (100 milliliters) then recovered via filtration. This extraction-filtration sequence is repeated two more times followed by drying in a vacuum oven at 80° C. and 1 mm Hg to provide a constant weight of 13.70 grams of pale tan colored crystalline product. Titration of a portion of the product reveals an epoxide equivalent weight of 205.2 (corrected for titrated contribution of the thiadiazole ring). Fourier transform infrared spectrophotometric analysis of a potassium bromide pellet of the product reveals the presence of absorptions at 1603, 1576, 1516, 1443 and 1410 cm$^{-1}$ characteristic of the aromatic ring and the thiadiazole ring, disappearance of the hydroxyl group O—H stretching centered at 3336 cm$^{-1}$, out-of-plane C—H bending vibration at 832 cm$^{-1}$ indicative of paradisubstitution and epoxide —C—O— stretching absorbance at 866 and 912 cm$^{-1}$. Differential scanning calorimetry scanning calorimetry of a portion of the product (13.0 milligrams) heated from 30° to 300° C. at 10° C. per minute under nitrogen flowing at 35 cubic centimeters per minute reveals a sharp melting point endotherm (84.8 joules per gram) with a minimum at 182.4° C. followed by an exotherm (534.8 joules per gram) with a maximum at 221.5° C. High pressure liquid chromatographic analysis using an ultraviolet absorbance detector reveals a single peak comprising 95.0 area % (molar absorptivity not determined) of the product, with the balance of the area contained in a pair of minor coproduct peaks.

C. Characterization of the Diglycidyl Ether of 2,5-(4-hydroxyphenyl)thiadiazole for Liquid Crystallinity Analysis of the diglycidyl ether of 2,5-(4-hydroxyphenyl)thiadiazole from B above via crosspolarized light microscopy is completed using a microscope equipped with a programmable hot stage with heating from 30° to 220° C. using a heating rate of 10° C. per minute. The results are reported in Table I.

TABLE I

| OBSERVED TRANSITION TEMPERATURE (°C.) | COMMENTS |
|---|---|
| 30 | Birefringent, crystalline solid. |
| 172 | First fluidity noted. |
| 184 | Liquid crystal phase forms with aggregated solid particles present. |
| 202 | Liquid crystal phase clears and solid particles dissolve as coverslip is moved to mix the sample. |
| 205 | Viscosity increases. |
| 220 | Thermosets to a non-birefringent solid. Low level of birefringence noted when cooled to 30° C. |

The diglycidyl ether is an enantiotropic liquid crystal. Analysis of a second portion of the diglycidyl ether of 2,5-(4-hydroxyphenyl)thiadiazole from B above via crosspolarized light microscopy is completed using a microscope equipped with a programmable hot stage preheated to 184° C. The results are reported in Table II.

TABLE II

| TIME at 184° C. (min.) | COMMENTS |
|---|---|
| 1 | Liquid crystal phase forms with aggregated solid particles present. |
| 2 | Solid particles dissolve as coverslip is moved to mix the sample, opalescent, liquid crystalline. |
| 10 | Solid particles have cleared, opalescent, liquid crystalline. |
| 12 | Viscosity increases, non-opalescent, non-birefringent. |
| 15 | Solidifies, begin cooling, highly birefringent, partially opaque solid with a microdomain appearance at 30° C. |

EXAMPLE 2

Preparation of a Blend of the Diglycidyl Ether of 2,5-(4-Hydroxyphenyl)thiadiazole and 2,5-(4-Hydroxyphenyl)thiadiazole and Copolymerization A portion (0.4575 gram, 0.00223 epoxide equivalent) of the diglycidyl ether of 2,5-(4-hydroxyphenyl)thiadiazole from Example 1-B and a portion (0.3013 gram, 0.02233 hydroxyl equivalent) of 2,5-(4-hydroxyphenyl)thiadiazole from Example 1-A are added to a ceramic mortar and ground to a homogeneous powder. Differential scanning calorimetry analysis of a portion (11.7 milligrams) of the powder blend heated at 10° C. per minute under nitrogen flowing at 35 cubic centimeters per minute reveals an exotherm (295.8 joules per gram) with a maximum at 175.5° C. Analysis of a portion of the powder blend via crosspolarized light microscopy is completed using a microscope equipped with a programmable hot stage with heating from 30° to 225° C. using a heating rate of 10° C. per minute. The results are reported in Table III.

TABLE III

| OBSERVED TRANSITION TEMPERATURE (°C.) | COMMENTS |
|---|---|
| 0 | Birefringent, crystalline solid. |
| 167 | First fluidity noted. |
| 179 | Powder has fused, highly birefringent liquid crystal phase forms. |
| 225 | Highly birefringent brown colored solid, begin cooling, highly birefringent opaque solid with crystalline appearance at 30° C. |

EXAMPLE 3

Analysis of Copolymerized Blend of Diglycidyl Ether of 2,5-(4-Hydroxyphenyl)thiadiazole and 2,5-(4-Hydroxyphenyl)thiadiazole for Glass Transition Temperature A portion (12.55 milligrams) gram of the diglycidyl ether of 2,5-(4-hydroxyphenyl)thiadiazole and 2,5-(4-hydroxyphenyl)thiadiazole blend from Example 2 are cured in a differential scanning calorimeter by heating at 10° C. per minute under a stream of nitrogen flowing at 35 cubic centimeters per minute to 170° C., followed by holding at this temperature for 20 minutes, heating at 10° C. per minute to 190° C., followed by holding at this temperature for 10 minutes, then heating at 10° C. per minute to 210° C., followed by holding at this temperature for 10 minutes. After gradual cooling to 30° C., a second scan is completed by heating from 30° to 300° C. at 10° C. per minute under nitrogen flowing at 35 cubic centimeters per minute. No events were detected up to a sharp exothermic rise with an onset at 245.4° C. Curing of a second sample (11.20 milligrams) of the blend is completed using the aforementioned time-temperature profile with the addition of heating at 10° C. per minute to 230° C. followed by holding at this temperature for 10 minutes, then 10° C. per minute to 250° C. followed by holding at this temperature for 10 minutes. Completion of a second scan using the aforementioned conditions revealed no events up to a sharp exothermic rise with an onset at 265.2° C.

EXAMPLE 4

A. Synthesis of 1,4-bis(4-methoxybenzoyl)hydrazide

4-Methoxybenzoyl chloride (75.0 gram, 0.44 mole) is dissolved in tetrahydrofuran (750 milliliters) then added to an addition funnel while maintained under a nitrogen atmosphere. Tetrahydrofuran (500 milliliters) and triethylamine (52.27 gram, 0.517 mole) are added to a two liter glass reactor equipped with a condenser, stirring, a nitrogen inlet, an inlet covered by a rubber septum, the reactant-containing addition funnel and a thermometer. Anhydrous hydrazine (6.73 grams, 0.21 mole) is added to the reactor via injection through the rubber septum. The reactor exterior is maintained in a methylene chloride bath, stirring commences under a nitrogen atmosphere and the reactants are cooled to 0° C. by addition of dry ice to the methylene chloride bath. Once the 0° C. temperature is established, the 4-methoxybenzoyl chloride-tetrahydrofuran solution is added dropwise to the reactor over a one hour period and at a rate so as to maintain the 0° C. reaction temperature. After completion of the addition, the slurry is stirred for an additional hour while maintaining the 0° C. temperature, followed by removal of the cooling bath and gradual warming to room temperature (23° C.). After stirring for four hours at room temperature, the reactor contents are filtered and the recovered crystals slurried in deionized water (100 milliliters) then recovered by filtration and dried under vacuum at 80° C. and 1 mm Hg to a constant weight of 28.83 grams of bright white crystalline needles. A second crop of crystals (3.14 grams) are recovered by rotary evaporation of the filtrate to a volume of 500 milliliters followed by cooling to room temperature, filtration and drying under vacuum. Fourier transform infrared spectrophotometric analysis of a potassium bromide pellet of the product reveals the presence of secondary hydrazide N—H stretching (solid state) at 3207 cm$^{-1}$, secondary hydrzide carbonyl stretching (solid state) at 1598 cm$^{-1}$ (combined as a double peak with aromatic ring absorption at 1609 cm$^{-1}$), the methoxy group C—H stretching at 2837 cm$^{-1}$ and the out-of-plane C—H bending vibration at 841 cm$^{-1}$ indicative of para-disubstitution. Proton magnetic resonance spectroscopy and $^{13}$carbon magnetic resonance spectroscopy further substantiated the product structure. High pressure liquid chromatographic analysis using an ultraviolet absorbance detector reveals a single peak comprising 99.1 area % (molar absorptivity not determined) of the product.

B. Synthesis of 2,5-(4-methoxyphenyl)oxadiazole 1,4-bis(4-Methoxybenzoyl)hydrazide (7.48 grams, 0.0249 mole) from B above and phosphorous oxychloride (250 grams) are added to a one liter glass reactor equipped with a glycol-water condenser chilled to 2° C., stirring, a nitrogen inlet flowing at a rate of one liter per minute and a thermometer-heating mantle-temperature controller assembly. Heating to a 106° C. reflux commences and after 16 hours at the 106° C. temperature, a distillation head is added between the reactor and the condenser and phosphorous oxychloride (200 milliliters) is then distilled from the reactor into a receiver. The solution remaining in the reactor is cooled to 50° C., then recovered and added to stirred deionized water (2 liters). After stirring for five minutes, the white crystalline product is recovered via filtration, washed in the filter with three 100 milliliter portions of deionized water, then dried under vacuum at 100° C. and 1 mm Hg to a constant weight of 6.76 grams. Fourier transform infrared spectrophotometric analysis of a potassium bromide pellet of the product reveals the presence of absorptions at 1609, 1589 (shoulder), 1490, 1437 and 1417 cm$^{-1}$ characteristic of the aromatic ring and the oxadiazole ring, the methoxy group C—H stretching centered at 2838 cm$^{-1}$ and the out-of-plane C—H bending vibration at 832 cm$^{-1}$ indicative of para-disubstitution. High pressure liquid chromatographic analysis using an ultraviolet absorbance detector reveals a single peak comprising 99.9 area % (molar absorptivity not determined) of the product.

C. Demethylation of 2,5-(4-methoxyphenyl)oxadiazole 2,5-(4-methoxyphenyl)oxadiazole (6.65 grams, 0.0471 methoxy equivalent), anhydrous lithium iodide (11.16 grams, 0.0834 mole) and 2,4,6-trimethylpyridine (35 milliliters) are added to a one liter glass reactor equipped with a glycol-water condenser chilled to 2° C., stirring, a nitrogen inlet flowing at a rate of one liter per minute and a thermometer-heating mantle-temperature controller assembly. The lithium iodide used was dried under vacuum at 175° C. and 1 mm Hg for 16 hours immediately prior to use herein. Heating and stirring of the slurry under a nitrogen atmosphere commences and once the temperature achieves 148° C., a solution forms. After an additional eight minutes of heating, a 170° C. reflux is achieved and the solution becomes hazy. After five minutes at reflux, crystals began to deposit on the walls of the reactor. After a total of 318 minutes at reflux (170° to 167° C.), the stirred crystalline slurry is cooled to 50° C., then dissolved in deionized water (100 milliliters). Once the solution is cooled to room temperature (23° C.), stirring of the solution commences, then concentrated aqueous hydrochloric acid (50 milliliters) is added. After stirring for two minutes, the white crystalline product is recovered via filtration, washed in the filter with three 100 milliliter portions of deionized water, then dried under vacuum at 80° C. and 1 mm Hg to a constant weight of 5.69 grams. Fourier transform infrared spectrophotometric analysis of a potassium bromide pellet of the product reveals the presence of absorptions at 1609, 1589 (shoulder), 1570 (shoulder), 1497, and 1437 cm$^{-1}$ characteristic of the aromatic ring and the oxadiazole ring, the hydroxyl group O—H stretching centered at 3163 cm$^{-1}$ and the out-of-plane C—H bending vibration at 837 cm$^{-1}$ indicative of para-disubstitution. Differential calorimetry scanning calorimetry of a portion of the product (10.3 milligrams) heated at 10° C. per minute under nitrogen flowing at 35 cubic centimeters per minute reveals a sharp melting point endotherm (87.0 joules per gram) with a minimum at 349.2° C.

D. Epoxidation of 2,5-(4-hydroxyphenyl)oxadiazole 2,5-(4-Hydroxyphenyl)oxadiazole (5.60 grams, 0.0441 hydroxyl equivalent) from A above, epichlorohydrin (407.7 grams, 4.4 moles) and tetrabutylammonium bromide (0.056 gram, 1.00 % wt. of the diphenol reactant used) are added to a one liter glass round bottom reactor and heated to 75° C. with magnetically driven stirring under a nitrogen atmosphere flowing at a rate of one liter per minute. The slurry becomes a clear solution after 428 minutes at the 75° C. reaction temperature. After 652 minutes at 75° C., high pressure liquid chromatographic analysis of a portion of the light amber colored solution demonstrates that complete conversion of the diphenol has occurred. At this time, a water separator is interspersed between the reactor and the chilled (−2.5° C.) glycol condenser and an addition funnel containing sodium hydroxide (1.98 grams, 0.0496 mole) dissolved in deionized (2.42 grams, 55% wt. of the solution) and a vacuum line are added to the reactor. The nitrogen purge is shut off simultaneous with initiation of the vacuum. The vacuum and reaction temperature are equilibrated at 70 mm Hg and 50° C., respectively and such that a vigorous reflux is maintained with continuous return of dry epichlorohydrin from the water separator to the reactor. After equilibration, dropwise addition of the aqueous sodium hydroxide commences. After 53 minutes, addition of the aqueous sodium hydroxide is complete. After an additional 2.75 hours at the 70 mm Hg vacuum and 50° C. reaction temperature, heating ceases, vacuum is released and the product slurry recovered. The recovered slurry is filtered through a bed of diatomaceous earth while still hot and the resultant light amber colored solution is then washed in a separatory funnel with deionized water (100 milliliters), dried over anhydrous sodium sulfate, then filtered. The recovered filtrate is rotary evaporated under a vacuum with heating to 90° C. The resultant powder is dried in a vacuum oven at 80° C. and 1 mm Hg to provide a constant weight of 5.51 grams of white crystalline product. Titration of a portion of the product reveals an epoxide equivalent weight of 187.4. Fourier transform infrared spectrophotometric analysis of a potassium bromide pellet of the product reveals the presence of absorptions at 1609, 1589 (shoulder), 1497, 1457, 1430 and 1423 (double peak) cm$^{-1}$ characteristic of the aromatic ring and the oxadiazole ring disappearance of the hydroxyl group O—H stretching centered at 3163 cm$^{-1}$, out-of-plane C—H bending vibration at 839 cm$^{-1}$ indicative of para-disubstitution and epoxide —C—O— stretching absorbance at 866 and 912 cm$^{-1}$. Differential scanning calorimetry of a portion of the product (13.0 milligrams) heated from 30° to 300° C. at 10° C. per minute under nitrogen flowing at 35 cubic centimeters per minute reveals a sharp melting point endotherm (128.7 joules per gram) with a minimum at 200.1° C. followed by an exotherm (370.0 joules per gram) with a maximum at 253.6° C. High pressure liquid chromatographic analysis using an ultraviolet absorbance detector reveals a single peak comprising 93.3 area % (molar absorptivity not determined) of the product, with the balance of the area contained in a single additional coproduct peak.

E. Characterization of the Diglycidyl Ether of 2,5-(4-hydroxyphenyl)oxadiazole for Liquid Crystallinity Analysis of a portion of the diglycidyl ether of 2,5-(4-hydroxyphenyl)oxadiazole from D above via crosspolarized light microscopy is completed using a microscope equipped with a programmable hot stage with heating from 30° to 243° C. using a heating rate of 10° C. per minute. The results are reported in Table IV.

TABLE IV

| OBSERVED TRANSITION TEMPERATURE (°C.) | COMMENTS |
| --- | --- |
| 30 | Birefringent, crystalline solid. |
| 187 | First fluidity noted. |
| 190 | Nematic liquid crystal fluid forms. |
| 195 | Isotropization. |
| 225 | Viscosity increases, opalescent fluid due to grainy birefringent microdomains forming. |
| 243 | Thermosets to opalescent solid with grainy birefringent microdomains. |

The diglycidyl ether is an enantiotropic liquid crystal.

EXAMPLE 5

Preparation of a Blend of the Diglycidyl Ether of 2,5-(4-Hydroxyphenyl)oxadiazole and 2,5-(4-Hydroxyphenyl)oxadiazole and Copolymerization A portion (0.1131 gram, 0.0006 epoxide equivalent) of the diglycidyl ether of 2,5-(4-hydroxyphenyl)oxadiazole from Example 4-D and a portion (0.0767 gram, 0.0006 hydroxyl equivalent) of 2,5-(4-hydroxyphenyl)oxadiazole from Example 4-C are added to a ceramic mortar and ground to a homogeneous powder. Differential scanning calorimetry analysis of a portion (9.60 milligrams) of the powder blend heated at 10° C. per minute under nitrogen flowing at 35 cubic centimeters per minute reveals an exotherm with multiple shoulders (103.5 joules per gram) and with a maximum at 197.6° C. A sharp exothermic rise with an onset at 267.5° C. is observed at the completion of the first exothermic event. Analysis of a portion of the powder blend via crosspolarized light microscopy is completed using a microscope equipped with a programmable hot stage preheated to 200° C. The results are reported in Table V.

TABLE V

| TIME at 200° C. (sec.) | COMMENTS |
| --- | --- |
| 12 | First fluidity noted. |
| 14 | Flows to a nematic liquid crystal fluid, some dispersed crystals present. |
| 22 | Fuses to a solid with nematic liquid crystal texture, highly birefrinqent. |

EXAMPLE 6

Analysis of Copolymerized Blend of Diglycidyl Ether of 2,5-(4-Hydroxyphenyl)oxadiazole and 2,5-(4-Hydroxyphenyl)oxadiazole for Glass Transition Temperature A portion (12.55 milligrams) gram of the diglycidyl ether of 2,5-(4-hydroxyphenyl)oxadiazole and 2,5-(4-hydroxyphenyl)oxadiazole blend from Example 5 is cured in a differential scanning calorimeter by heating at 10° C. per minute under a stream of nitrogen flowing at 35 cubic centimeters per minute to 220° C., followed by holding at this temperature for 20 minutes. After gradual cooling to 30° C., a second scan is completed by heating from 30° to 250° C. at 10° C. per minute under nitrogen flowing at 35 cubic centimeters per minute. No events were detected up to a sharp exothermic rise with an onset at 238.6° C.

EXAMPLE 7

A. Synthesis of 2,5-(3-hydroxyphenyl)thiadiazole p-Hydroxybenzaldehyde (24.99 grams, 0.205 mole), sulfur (13.14 grams, 0.41 mole), and ethylene glycol (300 milliters) are added to a one half liter glass reactor equipped with a condenser venting through a scrubber charged with aqueous sodium hydroxide solution, stirring, a nitrogen inlet flowing at a rate of one liter per minute, an addition funnel and a thermometer-heating mantle-temperature controller assembly. Hydrazine monohydrate (30.79 grams, 0.615 mole) is added dropwise to the reactor, followed by an aliquot of additional ethylene glycol (100 milliliters). After completion of the addition, heating to 105° C. commences with the reaction temperature initially overshooting to 120° C. After 65 hours at the 105° C. temperature, a slurry of crystals are observed in the reactor. The reaction mixture is cooled and the crystals allowed to settle, then recovered via filtration. The recovered crystals are added to a beaker and slurried in a minimum of cold (0° C.) ethanol and then refiltered. The crystals are recovered by filtration, reslurried in cold ethanol, then recovered by filtration and dried under vacuum at 80° C. and 1 mm Hg to a constant weight of 16.82 grams of pale yellow colored product. Fourier transform infrared spectrophotometric analysis of a potassium bromide pellet of the product reveals the presence of absorptions at 1609 (shoulder), 1589, 1530 (minor shoulder), 1497 (shoulder), 1463 (shoulder), 1443, 1423 (shoulder), and 1370 cm$^{-1}$ characteristic of the aromatic ring and the thiadiazole ring, the hydroxyl group O—H stretching centered at 3382 cm$^{-1}$ and the out-of-plane C—H bending vibration at 773 cm$^{-1}$ indicative of meta-disubstitution. Differential scanning calorimetry of a portion of the product (14.8 milligrams) heated at 10° C. per minute under nitrogen flowing at 35 cubic centimeters per minute reveals a sharp melting point endotherm (165.9 joules per gram) with a minimum at 286.2° C. Proton magnetic resonance spectroscopy and $^{13}$carbon magnetic resonance spectroscopy further substantiates the product structure. High pressure liquid chromatographic analysis using an ultraviolet absorbance detector reveals a single peak comprising 100 area % (molar absorptivity not determined) of the product.

B. Epoxidation of 2,5-(3-hydroxyphenyl)thiadiazole 2,5-(3-Hydroxyphenyl)thiadiazole (4.05 grams, 0.03 hydroxyl equivalent) from A above, epichlorohydrin (277.6 grams, 3.0 moles) and tetrabutylammonium bromide (0.0405 gram, 1.00% wt. of the diphenol reactant used) are added to a one liter glass round bottom reactor and heated to 75° C. with magnetically driven stirring under a nitrogen atmosphere flowing at a rate of one liter per minute. After 15 hours at 75° C., high pressure liquid chromatographic analysis of a portion of the light amber colored solution demonstrates that complete conversion of the diphenol has occurred. At this time, a water separator is interspersed between the reactor and the chilled (−2.5° C.) glycol condenser and an addition funnel containing sodium hydroxide (1.35 grams, 0.0338 mole) dissolved in deionized water (1.65 grams, 55% wt. of the solution) and a vacuum line are added to the reactor. The nitrogen purge is shut off simultaneous with initiation of the vacuum. The vacuum and reaction temperature are equilibrated at 117 mm Hg and 50° C., respectively and such that a vigorous reflux is maintained with continuous return of dry epichlorohydrin from the water separator to the reactor. After equilibration (5 minutes), dropwise addition of the aqueous sodium hydroxide commences. After 28 minutes, addition of the aqueous sodium hydroxide is complete. After an additional 2.5 hours at the 117 mm Hg vacuum and 50° C. reaction temperature, heating ceases, vacuum is released and the product slurry recovered. The recovered slurry is filtered through a bed of diatomaceous earth while still hot and the resultant light yellow colored solution rotary evaporated under a vacuum with heating to 90° C. The resultant solid product is allowed to cool to room temperature (23° C.), then suspended in acetone (40 milliliters) with mixing until a fine slurry forms. Deionized water (20 milliliters) is added to the slurry with mixing followed by filtration. The product removed by filtration is resuspended in acetone (40 milliliters) with mixing, diluted with deionized water (20 milliliters), then filtered, followed by drying of the product recovered on the filter in a vacuum oven at 80° C. and 1 mm Hg to provide a constant weight of 5.29 grams of pale tan colored crystalline product. Titration of a portion of the product reveals an epoxide equivalent weight of 220.5 (corrected for titrated contribution of the thiadiazole ring). Fourier transform infrared spectrophotometric analysis of a potassium bromide pellet of the product reveals the presence of absorptions at 1609 (shoulder), 1583, 1503 (shoulder), 1470, 1450 (shoulder), 1430, and 1370 (shoulder) cm$^{-1}$ characteristic of the aromatic ring and the thiadiazole ring, disappearance of the hydroxyl group O—H stretching centered at 3382 cm$^{-1}$, out-of-plane C—H bending vibration at 773 cm$^{-1}$ indicative of meta-disubstitution and epoxide —C—O— stretching absorbance at 859 and 919 cm$^{-1}$. Differential scanning calorimetry scanning calorimetry of a portion of the product (11.1 milligrams) heated from 30° to 300° C. at 10° C. under nitrogen flowing at 35 cubic centimeters per minute reveals a melting point endotherm (64.7 joules per gram) with a minimum at 112.3° C. followed by an exotherm (495.3 joules per gram) with a maximum at 234.8° C.

EXAMPLE 8

Preparation of a Blend of the Diglycidyl Ether of 2.5-(3-Hydroxyphenyl)thiadiazole and 4,4'-Diaminodiphenylsulfone A portion (0.3538 gram, 0.0016 epoxide equivalent) of the diglycidyl ether of 2,5-(3-hydroxyphenyl)-thiadiazole from Example 7-B and 4,4'-diaminodiphenylsulfone (0.0996 gram, 0.0016 —NH equivalent) are dissolved in methylene chloride (5 milliliters) then dried in a forced air, convection type oven at 50° C. Differential scanning calorimetry analysis of a portion (10.6 milligrams) of the powder blend heated at 10° C. per minute under nitrogen flowing at 35 cubic centimeters per minute reveals a melting point endotherm (45.7 joules per gram) with a maximum at 95.6° C. followed by an exotherm (343.8 joules per gram) with maximum at 203.4° C.

What is claimed is:

1. An advanced epoxy resin comprising the product of the advancement reaction of
   (A) at least one epoxy resin containing an average of more than one vicinal epoxide group per molecule and at least one thiadiazole, oxadiazole or both at least one thiadiazole and at least one oxadiazole moiety per molecule, said moieties comprising at least one —Ar—(X$^1$)$_n$—N—(X$^1$)$_n$—Ar— group, where Ar is a divalent aromatic group, X$^1$ is a divalent linking group selected from the group consisting of —O—, —S—, —SO—, —SO$_2$—, —CO—, —O—CO—, —CO—O—, —S—CO—, —CO—S—, —NH—CO—, —CO—NH—, —NR—CO—, —CO—NR—, —NH—CO—NH—, —NR—CO—NH—, —NH—CO—NR—, —NH—CO—O— and —O—CO—NH—, N is thiadiazole or oxadiazole, each R is independently a hydrocarbyl group having from one to about 10 carbon atoms and n is 0 or 1; with
   (B) at least one compound containing an average of more than one hydrogen atom per molecule reactive with a vicinal epoxide group, wherein component (A) and component (B) are present in an amount which provides a mole ratio of epoxide reactive hydrogen atoms in component (B) to epoxide groups in component (A) of from about 0.01:1 to about 0.94:1.

2. A curable composition comprising (I) the advanced epoxy resin of claim 1 and (II) a curing amount of at least one curing agent or at least one curing catalyst or both curing agent and curing catalyst therefor.

3. A product or article resulting from curing the curable composition of claim 2.

4. A product or article of claim 3 wherein said thiadiazole, oxadiazole or both a thiadiazole and an oxadiazole moiety are incorporated so as to form a mesogenic moiety which is oriented either prior to or during cure or both prior to and during cure.

5. A product of claim 4 wherein said orientation is induced by means of an electric field, magnetic field, or by drawing or shear forces, or a combination thereof.

6. A phenoxy resin comprising the product of the advancement reaction of
   (A) at least one epoxy resin containing an average of more than one vicinal epoxide group per molecule and at least one thiadiazole, oxadiazole or both thiadiazole and oxadiazole moiety per molecule, said moieties comprising at least one —Ar—(X$^1$)$_n$—N—(X$^1$)$_n$—Ar— group where Ar is a divalent aromatic group, X1, is a divalent linking group selected from the group consisting of —O—, —S—, —SO—, —SO$_2$—, —CO—, —O—CO—, —CO—O—, —S—CO—, —CO—S—, —NH—CO—, —CO—NH—, —NR—CO—, —CO—NR—, —NH—CO—NH—, —NR—CO—NH—, —NH—CO—NR—, —NH—CO—O— and —O—CONH—, where N is thiadiazole or oxadiazole, n is 0 or 1 and each R is independently a hydrocarbyl group having from one to about 10 carbon atoms, with
   (B) at least one compound containing an average of more than one hydrogen atom per molecule reactive with a vicinal epoxide group, wherein component (A) and component (B) are present in an amount which provides a mole ratio of epoxide reactive hydrogen atoms in component (B):epoxide groups in component (A) of from about 0.95:1 to about 1.05:1.

7. A product or article comprising the phenoxy resin of claim 6 wherein said thiadiazole, oxadiazole or both a thiadiazole and an oxadiazole moiety are incorporated so as to form a mesogenic moiety which is oriented.

8. A product of claim 7 wherein said orientation is induced by means of an electric field, magnetic field, or by drawing or shear forces, or a combination thereof.

* * * * *